United States Patent [19]

Hovorka et al.

[11] Patent Number: 4,791,069

[45] Date of Patent: Dec. 13, 1988

[54] METHODS FOR ATTACHING LIGANDS OR ANTI-LIGANDS TO A SOLID PHASE

[75] Inventors: George Hovorka, Milton; W. Peter Hansen, Middleboro, both of Mass.

[73] Assignee: Ortho Diagnostic Systems Inc., Raritan, N.J.

[21] Appl. No.: 47,826

[22] Filed: May 8, 1987

Related U.S. Application Data

[62] Division of Ser. No. 653,383, Sep. 21, 1984, Pat. No. 4,689,310.

[51] Int. Cl.$^4$ ........................................... G01N 33/531
[52] U.S. Cl. ..................... 436/533; 436/534; 436/535; 436/807; 436/809; 427/2
[58] Field of Search ............... 427/2; 436/501, 512, 436/515, 524, 528, 533, 534, 535, 807, 809

[56] References Cited

U.S. PATENT DOCUMENTS

| 3,074,853 | 1/1963 | Brewer | 436/807 |
| 4,338,094 | 7/1982 | Elahi | 436/535 |
| 4,487,839 | 12/1984 | Kamentsky | 436/809 |
| 4,672,024 | 6/1987 | Giaever | 427/2 |
| 4,748,042 | 5/1988 | Linnecke | 436/531 |

Primary Examiner—Robert J. Warden
Assistant Examiner—Robert Benson
Attorney, Agent, or Firm—Richard J. Grochala

[57] ABSTRACT

Methods for attaching one component of a ligand-antiligand pair onto a solid phase surface. The component may be attached to a photoactivatable cross-linker capable of coupling the component to a colloidal medium coating the surface or alternatively, the component may be coupled to a bead and held in place against the surface by an overlay of the colloidal media having voids and spaces smaller than the diameter of the particle but large enough to permit diffusion of the other of the ligand-anti-ligand pair to be detected.

18 Claims, No Drawings

METHODS FOR ATTACHING LIGANDS OR ANTI-LIGANDS TO A SOLID PHASE

This application is a division of U.S. Ser. No. 653,383, filed Sept. 21, 1984 now U.S. Pat. No. 4,689,310.

FIELD OF THE INVENTION

This invention relates to apparatus and methods for immobilizing one component of a ligand-anti-ligand pair on a solid phase surface and more particularly, provides solid phase components useful in immunoassays, particularly for those assays in which patterns are desired.

BACKGROUND OF THE INVENTION

The detection of specified antigens (defined as a substance whose introduction into an animal stimulates the production of antibodies capable of reacting specifically therewith), haptens (a substance requiring additional accessory materials before its introduction into an animal stimulates the production of antibodies specific therefor), and the like substances (hereinafter collectively referred to as ligands) in body fluids such as blood, sputum, urine and the like has in recent years become of utmost importance in both the research and clinical environments. The detection of ligands, particularly antigens or antibodies capable of specifically combining therewith (hereinafter collectively termed anti-ligands, which term is also meant to include antibody fragments such as F(ab), F(ab)'2 etc.) can often be related to various disease states and consequently is extremely useful in diagnosis, in gaining basic understandings concerning the genesis of disease, and in monitoring the effectiveness of therapies therefor.

The high level of specificity between ligands and antiligands has permitted the development of an entire class of assays typically referred to as immunoassays which are based on this immunological reaction or coupling therebetween. As will be readily appreciated by those skilled in the art, there are a great many ways in which immunoassays may be formatted depending upon whether the assays are to be performed simultaneously, in a forward or reverse direction, competitively, non-competitively, or in a homogeneous or heterogeneous manner as those terms and methods are readily understood and commonly practiced in the art.

One characteristic common to many of the foregoing types of assays, particularly those of the heterogeneous character, is the attachment of one of the components of a ligand-anti-ligand pair to a solid phase such as a plastic or glass surface, the surface of a microtiter tray, microparticle, paddle, etc. This solid phase or surface is typically inserted into the aqueous phase so as to allow detection of the aqueous sample complementary component of the ligand-anti-ligand pair by virtue of an immunological reaction occurring therebetween. Thus, following such a reaction, the aqueous component also becomes immobilized thereby allowing the substantial removal of both unreacted aqueous components and the concomitant associated background "noise" levels whose presence is generally deleterious to sensitivity.

Although a variety of schemes have been developed for the immobilization of ligand or anti-ligands onto a variety of solid phase surfaces, none have proved entirely satisfactory, often for reasons not altogether clear. Generally, attachment of the ligand or anti-ligand is preceded by some form of chemical manipulation such as the attachment of suitable groups for subsequent linkage onto the surface whereby washing steps or other mechanical manipulations do not result in their displacement. These chemical manipulations are, however, often deleterious to the immunological reactivity of the component and in certain circumstances, can actually render the component inactive thereby destroying its usefulness. Further, actual attachment of these ligand or anti-ligand components to the surface, whether by chemical or physical means, takes place in an unknown manner. Contemporary beliefs hold the components may actually attach in a spectrum of positions ranging from complete steric hindrance of the binding site, thereby preventing or significantly reducing reactivity, to unhindered access of the binding site. As may be expected, sensitivity of the assay declines with increasing levels of steric hindrance and loss of reactivity.

It is an object of the present invention to provide new methods for attaching a component of a ligand-anti-ligand pair which are less sensitive to steric orientation effects associated with prior methods and are accordingly more conveniently manufactured.

In one class of instruments useful with immunoassays such as that of Louis A. Kamentsky described in U.S. Ser. No. 455,765, now U.S. Pat. No. 4,487,839, entitled "Immunoassay Methods Employing Patterns For The Detection Of Soluble And Cell Surface Antigens", soluble antigens are reacted with antibodies which have been attached to a surface in a particular pattern. The pattern can be generally characterized as a repeating and alternating presence and absence of immunological reactivity. The repeated examination of areas having an immunological reaction and areas having an absence of such immunological reaction allows the subtraction of the latter area or background level from the test area and results in an instrument of great sensitivity. Of great importance to such an instrument is the accuracy and repeatability to which the anti-ligands are spatially resolved or patterned on the solid phase surface. Methods presently available to date are not sufficiently accurate when practiced on a commercial manufacturing scale to permit the production o such patterns in an acceptable and repeatable manner. Further, conventional methods for attaching anti-ligands or ligands, particularly immunoglobulins, to solid phase surfaces often disadvantageously results in short shelf-lifes thereby exacerbating production, shipment and storage difficulties.

It is another object of the present invention to provide methods which increase the shelf-life of the resultant solid phase component.

It is yet a further object of the present invention to provide methods of attachment whereby patterns may be produced having great repeatable accuracy and sharp lines of demarcation.

It is yet another object of the present invention to provide apparatus and methods useful in a variety of immunoassays, particularly with those based on pattern detections, which also permits commercial manufacture of such solid phase components in a repeatable and economical manner.

SUMMARY OF THE INVENTION

In accordance with the principles and objects of the present invention, there are provided solid phase components for use in immunoassays for detecting one component of a ligand-anti-ligand pair in an aqueous sample. The solid phase component comprises an insoluble surface with a material coated thereon operating in conjunction with means for insolubilizing the other of said ligand-anti-ligand pair on the surface. In a preferred embodiment, the coating is of a colloidal material and in the most preferred embodiment, comprises agarose.

The means for insolubilizing either the ligand or the anti-ligand to the surface comprises a photoactivatable cross-linker which is covalently coupled to either the colloidal material or the ligand (or anti-ligand) and which, upon suitable illumination, couples the ligand or anti-ligand to the surface. Alternately, the means for insolubilizing may comprise a micro or macroparticle of synthetic or natural origin (hereinafter collectively termed beads) having insolubilized thereon the ligand or anti-ligand component specific for the other component of the pair to be detected, i.e., the aqueous sample component. In this alternative preferred embodiment, the coated bead is held onto the insoluble surface by an overlay of the colloidal medium. The spaces or voids existing in the colloidal medium and the diameter of the beads are preferably adjusted so as to prevent the diffusion of the bead through the medium while allowing diffusion of the other of said ligand or anti-ligand component from said aqueous sample through the medium and to the insolubilized component on the bead.

Methods are also provided for the formation of such a solid phase component and generally set forth the preferred manner of their production in accordance with the preferred embodiments set forth above.

DETAILED DESCRIPTION AND BEST MODE

As will be readily appreciated, there are a tremendous variety of solid surfaces which may be utilized with the methods and principles of the instant invention. Such surfaces include for instance, microscope slides and other similar flat surfaces whether plastic or glass, the walls of microtiter type tray wells, tapes and disks such as those useful for synchronous pattern detection as disclosed in the Kamentsky U.S. Pat. No. 4,487,839, paddles and the like. Clearly, it will be readily apparent to those skilled in the art that various minor modifications to the methods of the instant invention may be required in order to fully utilize the inventive concepts described herein with the solid phase surface chosen. Such modifications will be well within the ability of the skilled investigator.

For purposes of the following discussion, it will be assumed that flat surfaces are being employed and immunologically active components are being associated therewith in a spatial pattern for use with the Kamentsky or similar instrument, it being understood that such an arrangement represents the most critical embodiment and that satisfying the needs of such an embodiment ensures satisfaction of other embodiments with less critical parameters. For instance, spatial patterns require sharp contrast demarcating the areas of presence or absence of the immunological component as opposed to those uses wherein spatial patterns are not being employed.

In the most preferred embodiment of the present invention, the insoluble surface is coated with a colloidal medium which firmly adheres to the surface. Such adherence should be of a degree suitable to withstand the rigors of subsequent immunological method steps such as washing and the like or other chemically related manipulations. Thereafter, the component of the ligand-anti-ligand pair which is to be immobilized, and having associated therewith a photoactivatable cross-linker, is brought into contact with the colloidal medium and subjected to illumination. As will be readily apparent, the illumination is spectrally chosen in order to activate the cross-linker whereby the immunological component becomes coupled to the colloidal medium and thus in turn immobilized. Any suitable cross-linking compound may be utilized such as psoralens, bleomycins, corticosteroids, porphyrins, pyrenes, acridines, organoplatinums and the like, or in the most preferred embodiment methyl-4-azidobenzoimidate in order to accomplish the goals of the present invention. Suitable as used herein means that the photoactivatable crosslinker can be coupled to the immunological component without substantially deleteriously affecting its immunological activity both before and subsequent to illumination. Further, it must be suitable in the sense that it is capable of reacting with the colloidal medium chosen in order to effect immobilization of the immunological component.

Presently, a colloidal medium is preferred as it is believed by the inventors hereof that the voids and channels provided therein may facilitate the diffusion of the immunological component therethrough. Pursuant to this theory, the immunological component to be immobilized may, prior to photoactivation diffuse through the voids and channels and become oriented in a variety of physical directions thereby facilitating physical access by its binding partner to the binding site. Alternatively, another medium having little or no colloidal spaces may be used in substitution to the aforedescribed colloidal medium whereby the immunological component, via photoactivatable cross-linker is attached predominantly on the surface and preferably so that the binding site is readily available to the aqueous binding partners.

It is further contemplated by the inventors hereof, and as will be readily appreciated by those skilled, that the immunological component may itself be readily modified such as by employment of an antibody fragment including for instance the F(ab) or F(ab)'$_2$ fragments or the like and indeed, immunologically active peptides (artificially created proteins) may be employed in substitution to the ligands or anti-ligands described previously.

Alternatively, the immunological component to be immobilized may itself be attached to a bead such as a microsphere, macrosphere, particle or other such polymer of either synthetic or naural origin. Numerous such beads have been described and are in conventional use in immunoassays as are the methods suitable for attaching immunological components thereto. Accordingly, those well-known details need not be reviewed herein.

Such immunologically active beads have been used primarily in heterogeneous type immunoassays since they readily lend themselves to separation via centrifugation or filtering techniques. The methods of the present invention capitalize on these well-known techniques by applying the bead immobilized, immunological components directly to the solid phase surface of the instant invention. The beads may be suitably applied by a variety of schemes including painting, spraying including such methods as are employed with ink jet printing and the like, and printing techniques such as those used with silk-screens. All such techniques provide reasonably well defined areas of application and by utilizing beads, the handling of the "printing medium" is greatly facilitated. Further, as is well-known by those who commonly employ beads, such can be commercially produced fairly easily and in a statistically very repeatable manner. Thereafter, the aforedescribed colloidal medium is used to coat the beads and by virtue of its adherence to the solid phase immobilizes the beads since they are ideally selected to be larger than the voids or channels of the colloidal medium.

The foregoing principles, procedures and teachings of the instant invention will be more readily understood by reference to the accompanying examples.

EXAMPLE 1

Creation of Synchronous Detection Patterns with Beads and Agarose

Ten micron glass microspheres (Polyscience #7668) were coated with mouse IgG, serving as an antigen, via covalent attachment generally pursuant to the procedures set forth in "Immobilized Enzymes" by O. R. Zabosrsky, CRC Press (1973). The coated microspheres were suspended in phosphate buffered saline (PBS), and pipetted onto glass slides into a spatially resolved pattern. The pattern was allowed to dry, almost to completion, at which point low melting point agarose (Sigma #A-4018) was overlaid each microsphere coated area using a micropipette. Only enough agarose was introduced to result in a coating approximately 50 microns thick. Reactivity was monitored using fluorescently labeled sheep anti-mouse IgG and fluorescence detected by a fluorescence sensitive photodetector.

EXAMPLE 2

Screen Printing Method of Creating Patterns

Screen printing methods have also been used to create immunologically reactive patterns. In this method a positive of the spatially resolved pattern was created on a piece of Kodak Plus-X Pan photographic film and developed using conventional means. The resultant image was then transferred to a photosensitized emulsion (Hunt #4533) which had been painted onto a 12X nylon mesh screen. Using the methods of screen development and exposure described in "Photographic Screen Printing" by A. Kosloff, Sign of the Times Publishing Company (1977), a negative of the image was formed on the screen. Microspheres prepared pursuant to the methods of Example 1 were then mixed into a 1% agarose solution. Using the screen which had been fitted into a conventional screen press, this preparation was then "printed" onto a warmed (40° C.) solid substrate which, upon cooling to room temperature, provided the desired pattern. Similar patterns derived via hand painting have shown the components to be immunologically reactive.

EXAMPLE 3

Photometrically Attaching Active Antibodies to a Solid Support in a Pattern

Two monoclonal antibodies to human chorionic gonadotropin (HCG), 10A5H7 and 5A4D10, were contained in ascites fluid obtained from Ortho Diagnostic Systems Inc., Raritan, N.J., and purified on a DEAE Affi-Gel Blue column [Bruck, C. et al., J. Immunol. Methods 53:313-319 (1982)]. A portion of each purified antibody was conjugated to the photoactivatable crosslinker methyl-4-azidobenzoimidate (MABI) by modifications of the methods of Ji and Sutoh [Ji, T. H., J. Biol. Chem. 252:1566-1570 (1977) and Sutoh, K., Biochemistry 19:1977-1983 (1980)].

Heated, liquified agarose in a 1% solution was poured into petri dishes and then poured out leaving a thin surface layer which was allowed to gel and dry. A 0.5 mg/ml solution of each of the purified antibodies with attached MABI was individually contacted to the dried agarose surface layer in separate petri dishes for a period of one hour. After this time the antibody solution was poured off and selected portions of the surface layer were exposed to ultraviolet light from a mercury discharge lamp. The agarose surface, layer was then washed in a PBS solution with 1% BSA (bovine serum albumin) overnight.

The activity of the antibodies in and on the agarose surface in the petri dish was assessed with Kamentsky-type prototype apparatus. Light at 488 nm from an argon ion laser was directed toward one area of the agarose surface layer in a petri dish. The fluorescence around 520 nm from the illuminated region was selected by interference filters, collected by a lens and converted to an electrical voltage by a photomultiplier. The fluorescent intensity from those portions which had been selectively exposed to ultraviolet light was electronically compared to the fluorescent intensity from those portions which had not been exposed to ultraviolet light.

Fluorescein isothiocyanate (FITC) was conjugated to HCG by adding a freshly prepared solution of FITC in 1.0 M pH 9.5 Na2C03-NaHC03 buffer to a solution of HCG in 0.02 M NaHC03 in a 50:1 FITC:HCG ratio. The mixture was incubated at 4° C. overnight and free FITC was rmmoved by dialysis.

The FITC conjugated HCG was added to the petri dish and the electronic signal derived from the differential binding of HCG to the regions on the petri dish which had been or had not been exposed to ultraviolet light was monitored using a Kamentsky type apparatus employing a chart recorder. There was a rapid rise in the electronic signal indicating that a significantly larger portion of the FITC conjugated HCG attached to those regions which had been exposed to the ultraviolet light than attached to those regions which had not been exposed to the ultraviolet light.

Control experiments were done on plates which were not incubated with the antibodies and they indicated no such rapid rise in electronic signal. Immunological controls were done by adding competing antibodies into the petri dish. It was found that a 3.5 ug/ml solution of 10A5H7 inhibited the development of an electronic signal from FITC conjugated HCG in a petri dish which had been incubated with MABI conjugated 10A5H7 antibody. No such inhibition occurred from the same concentration of 10A5H7 antibody in a petri dish which had been incubated with 5A4D10 antibody. These two antibodies were shown to be directed at two noncompeting epitopic sites on HCG by a sandwich ELISA assay.

What is claimed is:

1. A method for preparing a solid phase component useful in an immunoassay based on pattern detection, wherein a first member of a ligand-anti-ligand pair present in an aqueous sample is detected by reaction with a second member of the pair present on said insoluble surface in a spatial pattern, the method comprising the steps of:
   (a) providing said insoluble surface;
   (b) providing beads having attached thereto said second member;

(c) placing said beads on said surface in a resolved spatial pattern of repeating and alternating presence and absence of immunological reactivity; and (d) coating said beads and said surface with a gel, said gel having voids and channels which allow said first member to diffuse through the gel but not said beads, whereby said beads are maintained on said surface and said first component in said sample can diffuse through the gel to said second component and react immunologically therewith.

2. A method for preparing a solid phase component useful in an immunoassay based on pattern detection, wherein a first member of a ligand-anti-ligand pair present in an aqueous sample is detected by reaction with a second member of the pair present on an insoluble surface in a spatial pattern, the method comprising the steps of:

(a) providing said insoluble surface;

(b) providing beads having attached thereto said second member;

(c) coating said surface with a gel, said gel having voids and channels which allow said first member to diffuse through the gel, but not said beads;

(d) placing said beads in said gel in a resolved spatial pattern of repeating and alternating presence and absence of immunological reactivity, whereby said beads are maintained on said surface and said first component in said sample can diffuse through the gel to said second component and react immunologically therewith.

3. The method of claim 1, wherein the beads are placed by painting, spraying or printing.

4. The method of claim 3, wherein the beads are placed by ink jet printing, airbrushing or silk-screening.

5. The method of claim 1, wherein the ligand is an antigen and the anti-ligand is an antibody specific therefor.

6. The method of claim 1, wherein the anti-ligand is an antibody fragment.

7. The method of claim 6, wherein the antibody fragment is an F(b) or F(ab)'2 fragment.

8. The method of claim 1, wherein the insoluble surface is a plastic or glass flat surface.

9. The method of claim 8, wherein the surface is a microscope slide.

10. The method of claim 1, wherein the insoluble surface is the wall of a microtiter tray well.

11. The method of claim 1, wherein the gel is a polysaccharide gel.

12. The method of claim 11, wherein the gel is agarose.

13. The method of claim 1, wherein said gel is about 50 microns in thickness.

14. The method of claim 1, wherein the beads are constructed of a polymer of synthetic or natural origin.

15. The method of claim 14, wherein the beads are microspheres or macrospheres.

16. The method of claim 1, wherein the beads are glass microspheres.

17. The method of claim 1, wherein the second member is covalently attached to said beads.

18. The method of claim 2, wherein before step (d) the beads are mixed into a solution of said gel and then are placed in said gel as in step (d).

* * * * *